United States Patent [19]

Dingerdissen et al.

[11] Patent Number: 5,290,932
[45] Date of Patent: Mar. 1, 1994

[54] PREPARATION OF AMINES BY REDUCTIVE AMINATION USING ZEOLITE CATALYST

[75] Inventors: Uwe Dingerdissen, Seeheim-Jugenheim 1; Wolfgang Hoelderich, Frankenthal, both of Fed. Rep. of Germany

[73] Assignee: BASF Aktiengesellschaft, Ludwigshafen, Fed. Rep. of Germany

[21] Appl. No.: 969,730

[22] Filed: Oct. 30, 1992

[30] Foreign Application Priority Data

Nov. 11, 1991 [DE] Fed. Rep. of Germany ....... 4137013

[51] Int. Cl.$^5$ .................. C07D 295/02; C07D 205/04
[52] U.S. Cl. .................................... 544/178; 548/950;
548/579; 548/517; 548/518; 546/192; 546/208;
546/186; 546/349; 544/78; 544/129; 544/141;
540/480; 540/481; 540/450; 540/484
[58] Field of Search ............... 540/612, 484, 450, 480,
540/481, 602, 596, 597; 546/349, 350, 192, 208,
186; 548/578, 950, 579, 946; 544/78, 178, 129,
141

[56] References Cited

U.S. PATENT DOCUMENTS 3,903,079  9/1975  Heinz .............................. 260/293.51
3,976,697  0/1976  Kuntschik et al. ................. 260/583
4,806,690  0/1989  Bowman .............................. 564/480

FOREIGN PATENT DOCUMENTS 3116395  5/1982  Fed. Rep. of Germany .
9110641  11/1991  PCT Int'l Appl. .

OTHER PUBLICATIONS

Barney, Tetrahedron Letters, vol. 31, No. 39, pp. 5547-5550 (1990).
Organic Reactions, vol. 4, Chapter 3, (1948) pp. 174-256.
Houben-Weyl, Methoden der organischen Chemie, 4th Edition, vol. 11/1 (1957) pp. 611-663.
Database WPIL, Week 8815, Derwent Publications Ltd., AN 88-101677, Abstract of JP63051362.

Primary Examiner—Mukund J. Shah
Assistant Examiner—Pavanaram K. Sripada
Attorney, Agent, or Firm—John H. Shurtleff

[57] ABSTRACT

Amines of the general formula I

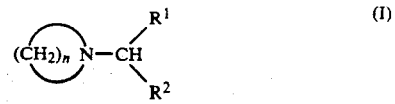
(I)

where $R^1$ and $R^2$ are each $C_1$-$C_{20}$-alkyl, $C_3$-$C_{20}$-cycloalkyl, $C_4$-$C_{20}$-alkylcycloalkyl, $C_4$-$C_{20}$-cycloalkylalkyl, aryl, $C_7$-$C_{20}$-alkylaryl, $C_7$-$C_{20}$-aralkyl or a heterocyclic radical and n is an integer of from 3 to 7, are prepared by a process in which a ketone of the general formula II

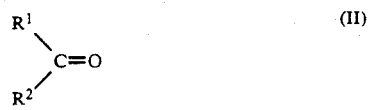
(II)

where $R^1$ and $R^2$ have the abovementioned meanings, is reacted with a cyclic amine of the general formula III

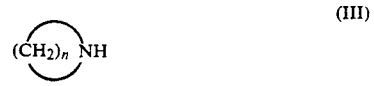
(III)

where n has the abovementioned meanings, in the presence of a zeolite and/or $SiO_2$ having a zeolite structure and/or a phosphate and/or a phosphate having a zeolite structure as catalysts at from 50° to 500° C. and from 0.01 to 50 bar.

13 Claims, No Drawings

PREPARATION OF AMINES BY REDUCTIVE AMINATION USING ZEOLITE CATALYST

The present invention relates to a process for the preparation of amines by reductive amination of ketones.

The preparation of tertiary amines by reductive amination is known from Organic Reactions, Vol. 4, Chapter 3, (1948) pages 174–256, or Houben-Weyl, Methoden der organischen Chemie, 4th Edition, G. Thieme Verlag Stuttgart, Vol. 11/1 (1957), pages 611 to 663. The reductive amination is carried out by reacting the ketone or aldehyde with the amine and hydrogen in the presence of a metal-containing catalyst. The metallic component of the catalyst may be, for example, nickel, platinum or palladium. In Organic Reactions, it is stated in particular that platinum is most suitable as a catalyst for the reaction of ketones having a low molecular weight with amines having a low molecular weight. According to this publication yields of up to 47% of theory are achieved in the reaction of secondary amines with ketones over a platinum catalyst.

In DE-A 25 35 725, reductive amination is carried out in the liquid phase over a supported nickel catalyst. Here, amine yields of up to 96% are achieved in the medium pressure range. The process is carried out in the liquid phase and has very long residence times (from 3 to 10 hours) and hence a low space/time yield.

The processes known to date have the disadvantage that low yields and/or long residence times have to be accepted.

It is an object of the present invention to remedy the abovementioned disadvantages.

We have found that this object is achieved by a novel and improved process for the preparation of amines of the general formula I

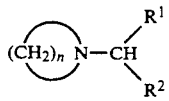

where $R^1$ and $R^2$ are each $C_1$–$C_{20}$-alkyl, $C_3$–$C_{20}$-cycloalkyl, $C_4$–$C_{20}$-alkylcycloalkyl, $C_4$–$C_{20}$-cycloalkylalkyl, aryl, $C_7$–$C_{20}$-alkylaryl, $C_7$–$C_{20}$-aralkyl or a heterocyclic radical and n is an integer of from 3 to 7, where a ketone of the general formula II

where $R^1$ and $R^2$ have the abovementioned meanings, is reacted with a cyclic amine of the general formula III

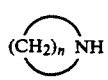

where n has the abovementioned meanings, in the presence of a zeolite and/or $SiO_2$ having a zeolite structure and/or a phosphate and/or a phosphate having a zeolite structure as catalysts at from 50° to 500° C. and from 0.01 to 50 bar.

The novel process for the preparation of amines I can be carried out as follows:

The reaction is effected by bringing the mixture of a ketone II and an amine III into contact with a zeolite and/or $SiO_2$ having a zeolite structure and/or a phosphate and/or a phosphate having a zeolite structure as catalysts of from 50° to 500° C. and from 0.01 to 50 bar.

The reaction can be carried out both in the liquid phase (suspension, trickle-bed or liquid-phase procedure) at from 50° to 200° C. and from 0.05 to 5 bar and, preferably, in the gas phase at from 100° to 500° C., preferably from 200° to 400° C., and from 0.01 to 50, preferably from 0.1 to 30, particularly preferably from 0.5 to 5, bar, batchwise or, preferably, continuously. The space velocity WHSV should as a rule be from 0.1 to 20, preferably from 0.5 to 5, $h^{-1}$ (g of starting mixture per g of catalyst per hour).

The process is generally carried out at atmospheric pressure or, depending on the volatility of the starting compound, at reduced or superatmospheric pressure (see above).

Sparingly volatile or solid starting materials II or III are used in dissolved form, for example in solution in tetrahydrofuran, toluene and/or petroleum ether. In general, dilution of the starting materials II or III with such solvents or with inert gases, such as $N_2$, Ar or steam, is possible.

After the reaction, the resulting products are isolated from the reaction mixture by a conventional method, for example by distillation; unconverted starting mixture is, if required, recycled to the novel reaction.

In a particularly preferred embodiment, the gaseous reaction products are introduced into a separation stage directly (immediately) after leaving the reactor and are then separated into their individual components. Separation of this type can be carried out, for example, in a fractionation column. This is advisable for suppressing the reverse reaction and for achieving a high conversion.

Acidic zeolite catalysts are used as catalysts for the novel process. Zeolites are crystalline aluminosilicates which have a highly ordered structure with a rigid three-dimensional network of $SiO_4$ and $AlO_4$ tetrahedra which are linked by common oxygen atoms. The ratio of Si and Al atoms to oxygen is 1 : 2 (cf. Ullmanns Encyclopadie d. techn. Chemie, 4th Edition, Volume 24, (1983) page 575. The electrovalency of the aluminum-containing tetrahedra is balanced by the inclusion of cations in the crystal, for example of an alkali metal or hydrogen ion. Cation exchange is possible. The voids between the tetrahedra are occupied by hydrogen molecules prior to dehydration by drying or calcination.

In the zeolites, instead of aluminum other elements such as B, Ga, Fe, Cr, Ti, V, As, Sb, Bi or Be or mixtures thereof, may also be incorporated in the lattice, or the silicon may be replaced with a tetravalent element, such as Ge, Ti, Zr or Hf.

Depending on their structure, zeolites are divided into different groups (cf. Ullmanns Encyclopädie d. techn. Chemie, 4th Edition, Vol. 24, (1983) page 575). Thus, the zeolite structure is formed by chains of tetrahedra in the mordenite group or by sheets of tetrahedra in the chabasite group, while in the faujasite group the tetrahedra are arranged to form polyhedra, for example in the form of a cubo-octahedron which consists of fourmembered rings or six-membered rings. Depending on the bonding of the cubo-octahedra, resulting in voids and pores of different sizes, a distinction is made between zeolites of the A, L, X or Y type. Catalysts suitable for the novel process are zeolites of the mordenite group or narrow-pore zeolites of the erionite or chabasite type or zeolites of the faujasite type, for example Y-, X-, beta- or L-zeolites. This group of zeolites includes the ultrastable zeolites of the faujasite type, ie. dealuminated zeolites. Processes for the preparation of such zeolites are described in Catalysis by Zeolites, Volume 5, from Studies in Surface Science and Catalysis, ed. B. Imelik et al., Elsevier Scientific Publishing Comp. 1980, page 203, and Crystal Structures of Ultra-stable Faujasites, Advances in Chemistry Series No. 101, American Chemical Society Washington, DC, (1971) page 226 et seq. and in U.S.-A-4,512,961.

Zeolites of the pentasil type (MFI structure; G. T. Kokotailo and W. M. Meier, Spec. Publ. Chem. Soc. 33 (1980), 133) are particularly advantageous.

They have, as a common base building block, a five-membered ring consisting of $SiO_4$ tetrahedra. They possess a high $SiO_2/Al_2O_3$ ratio and pore sizes which are between those of the zeolites of the A type and those of the X or Y type (cf. Ullmanns Encyclopädie d. techn. Chem., 4th Edition, Vol. 24, 1983).

These zeolites can have different chemical compositions. They are aluminosilicate, borosilicate, ferrosilicate, gallosilicate, chromosilicate, arsenosilicate, antimonosilicate and bismuth silicate zeolites or mixtures thereof, as well as aluminogermanate, borogermanate, gallogermanate and ferrogermanate zeolites or mixtures thereof or titanosilicate zeolites, such as TS-1, ETS 4 and ETS 10.

The aluminosilicate, borosilicate, gallosilicate and ferrosilicate zeolites of the pentasil type are particularly suitable for the novel process.

The aluminosilicate zeolite is prepared, for example, from an aluminum compound, preferably $Al(OH)_3$ or $Al_2(SO_4)_3$, and a silicon component, preferably finely divided silica, in aqueous amine solution, in particular in a polyamine, such as 1,6-hexanediamine or 1,3-propanediamine or triethylenetetramine solution, with or, in particular, without the addition of an alkali or an alkaline earth at from 100° to 220° C. under autogenous pressure. Such zeolites include the isotactic zeolites according to EP-A-34 727 and EP-A-46 504. The aluminosilicate zeolites obtained have an $SiO_2/Al_2O_3$ ratio of from 10 to 40,000, depending on the choice of the amount of starting materials. Such aluminosilicate zeolites can also be synthesized in an ether medium, such as diethylene glycol dimethyl ether, in an alcoholic medium, such as methanol or 1,4-butanediol, or in water.

The borosilicate zeolite is synthesized, for example, at from 90° to 200° C. under autogenous pressure by reacting a boron compound, eg. $H_3BO_3$ with a silicon compound, preferably finely divided silica, in aqueous amine solution, in particular in 1,6-hexanediamine or 1,3-propanediamine or triethylenetetramine solution, with or, in particular, without the addition of an alkali or alkaline earth. These zeolites include the isotactic zeolites according to EP-A-34 727 and EP-A-46 504. Such borosilicate zeolites can also be prepared if the reaction is carried out in solution in an ether, eg. diethylene glycol dimethyl ether, or in alcoholic solution, eg. 1,6-hexanediol, instead of in aqueous amine solution.

The gallosilicate zeolite of the pentasil type is synthesized, for example, at from 90° to 200° C. under autogenous pressure by reacting a gallium compound, for example an alkali metal gallate, preferably sodium gallate, or a gallium oxide or gallium halide or another suitable gallium salt, with a silicon compound, for example an alkali metal silicate, a silica sol, a silicic ester or, preferably, finely divided silica, in aqueous amine solution, for example in a primary, secondary or tertiary amine or quaternary alkylammonium compound, where one or more amine functions may be present per molecule, for example in 1,6-diaminohexane solution or in particular tetrapropylammonium hydroxide solution, with or without the addition of an alkali or an alkaline earth. The preparation of the zeolites in the presence of these amines is described in, for example, U.S.-A-3,702,886, BE-A-886 833, BE-A-882 484 and DE-A-30 06 471.

The ferrosilicate zeolite is obtained, for example, from iron compound, preferably $Fe_2(SO_4)_3$ and a silicon compound, preferably finely divided silica, in aqueous amine solution, in particular 1,6-hexanediamine, with or without the addition of an alkali or alkaline earth, at from 100° to 220° C. under autogenous pressure.

The suitable silicon-rich zeolites ($SiO_2/Al_2O_3 > 10$) include the ZSM types, beta-zeolite, ferrierite, EU-1, NU-1 and silicalits (a molecular sieve, a silica polymorph), ie. $SiO_2$ phases having a pentasil structure, whose characteristics and a process for whose preparation are described in, for example, DE-A-27 51 443 (US-A-4,061,724) and EP-A-64 372, EP-A-93 476 and EP-A-123 060.

The ultrastable zeolites, for example those of the faujasite type or mordenite type, ie. dealuminated Y-zeolites or dealuminated mordenite, whose preparation is described, for example, in US-A-4 512 961 and in H. K. Beyer and S. Belenykaja, Stud. Surf. Sci. Catal. 5 (1980), 203-209 and in I. M. Newsam, Science, 231 (1986), 1094, can also be used for the novel process.

The beta-zeolite as described in, for example, US-A-4,891,458 can also advantageously be used for the novel reaction.

Titanosilicates having a pentasil structure, for example TS-1, which are described, for example, by B. Kraushaar and I.H.C. van Haaff in Catalysis Letters 1 (1988), 81-89 or G. Perego et al. in Stud. Surf. Sci. Catal. 28 (1986), 129-136, are also suitable. The ETS molecular sieves, for example ETS-1, ETS-4 and ETS-10 (US-A-4,853,202 and ZA 88 09 457), can also be used.

The aluminosilicate, gallosilicate, borosilicate, titanosilicate and ferrosilicate zeolites or silicalits thus prepared can be isolated, dried at from 100° to 160° C., preferably 110° C. and calcined at from 450° to 550° C., preferably 500° C., before being molded with a binder in weight ratio of from 90 : 10 to 40 : 60 to give extrudates or pellets. Suitable binders are various aluminas, preferably boehmite, amorphous aluminosilicates having an $SiO_2/Al_2O_3$ ratio of from 25 : 75 to 90 : 5, preferably 75 : 25, silica, preferably finely divided $SiO_2$, mixtures of finely divided $SiO_2$ and finely divided $Al_2O_3$, $TiO_2$, $ZrO_2$ and clay. After the molding process, the extrudates or pellets are dried at 110° C. for 16 hours and calcined at 500° C. for 16 hours.

Advantageous catalysts are also obtained if the zeolites isolated, such as the aluminosilicate or borosilicate zeolite, are molded directly after drying and are not subjected to calcination until after the molding process. For example, the aluminosilicate and borosilicate zeolites prepared can also be used in pure form, without a binder, as extrudates or pellets, the extrusion or peptizing assistants used being, for example, ethylcellulose, stearic acid, potato starch, formic acid, oxalic acid, acetic acid, nitric acid, ammonia, amine, silicoesters and graphite or mixtures thereof.

If, owing to its method of preparation, the zeolite is not in the acidic H form but, for example, in the Na form, the latter can be converted completely or partially in the desired H form by ion exchange, for example with ammonium ions, and subsequent calcination or by treatment with acids.

If deactivation due to coking occurs during the novel use of the zeolite catalysts, it is advisable to regenerate the zeolites by burning off the coke deposit with air or with an air/$N_2$ mixture at from 400° to 550° C., preferably 500° C. The zeolites thus regain their initial activity.

By precoking, it is possible to adjust the activity of the catalyst for optimum selectivity of the desired reaction product.

To achieve very high selectivity, high conversion and long lives, it is advantageous to modify the zeolites.

In a suitable method for modifying the catalysts, for example, the unmolded or molded zeolites are doped with metal salts by ion exchange or by impregnation. Metals used are alkali metals, such as Li, Cs or K, alkaine earth metals, such as Mg, Ca or Sr, metals of the 3rd, 4th and 5th main groups, such as Al, Ga, Ge, Sn, Pb or Bi, transition metals of the 4th to 8th subgroups, such as Ti, Zr, V, Nb, Cr, Mo, W, Mn, Re, Fe, Ru, Os, Co, Rh, Ir, Ni, Pd or Pt, transition metals of the 1st and 2nd subgroups, such as Cu, Ag or Zn, and rare earth metals, such as La, Ce, Pr, Nd, Fr, Yb and U. In particular, the elements Pd, Pt, Rh, Ru, Re, Co, Cu, Zr, Fe, Ag, Zn, Mo and W are used for the novel process.

The doping is advantageously carried out by a procedure in which, for example, the molded zeolite is initially taken in a riser tube and, for example, an aqueous on ammoniacal solution of a halide or of a nitrate or the metals described above is passed over at from 20° to 100° C. Ion exchange of this type can be carried out, for example, over the hydrogen, ammonium and alkali metal forms of the zeolite. Another possible method for applying metals to the zeolite is to impregnate the zeolite material, for example with a halide, a nitrate or an oxide of the metals described above, in aqueous, alcoholic or ammoniacal solution. Both ion exchange and impregnation are followed by at least one drying step or a further calcination.

In a possible embodiment, for example, $Cu(NO_3)_2.3H_2O$ or $Ni(NO_3)_2.6H_2O$ or $Ce(NO_3)_3.6H_2O$ or $La(NO_3)_2. 6H_2O$ or $Cs_2CO_3$ is dissolved in water. The molded or unmolded zeolite is impregnated with this solution for a certain time, about 30 minutes. Any supernatant solution is freed from water in a rotary evaporator.

The impregnated zeolite is then dried at about 150° C. and calcined at 550° C. This impregnation process can be carried out several times in succession in order to obtain the desired metal content.

It is also possible, for example, to prepare an aqueous $Ni(NO_3)_2$ solution or ammoniacal $Pd(NO_3)_2$ solution and to suspend the pure zeolite in powder form therein at from 40° to 100° C. while stirring for about 24 hours. After the resulting zeolite material is filtered off, dried at about 150° C. and calcined at about 500° C., it can be further processed with or without a binder to give extrudates, pellets or fluidizable material.

Ion exchange of the zeolite in the H form or ammonium form or alkali form can be carried out by a procedure in which the zeolite, in the form of extrudates or pellets, is initially taken in a column and, for example, an aqueous $Ni(NO_3)_2$ solution or ammoniacal $Pd(NO_3)_2$ solution is circulated over it at slightly elevated temperatures of from 30° to 80° C. for from 15 to 20 hours. Thereafter, thorough washing with water, drying at about 50° C. and calcination at about 550° C. are carried out. In the case of some metal-doped zeolites, for example Pd-, Cu- and Ni-doped zeolites, an aftertreatment with hydrogen is advantageous.

In another possible method of modification, the molded or unmolded zeolite material is subjected to a treatment with acids, such as hydrochloric acid, hydrofluoric acid and phosphoric acid, and/or steam. In an advantageous procedure of this type, for example, zeolites in powder form are treated with 1 N phosphoric acid for 1 hour at 80° C. After the treatment, they are washed with water, dried at 110° C. for 16 hours and calcined at 500° C. for 20 hours. In another procedure, zeolites are treated, before or after they have been molded with binders, with a 3-25, in particular 12-20, % strength by weight aqueous hydrochloric acid, for example for from 1 to 3 hours at from 60° to 80° C. The zeolite treated in this manner is then washed with water, dried, and calcined at from 400° to 500° C.

In a particular embodiment of the acid treatment, the zeolite material, before it has been molded, is treated at elevated temperatures with hydrofluoric acid, which is generally used as 0.001 to 2 N, preferably 0.05 to 0.5 N, hydrofluoric acid, for example by refluxing for in general from 0.5 to 5, preferably from 1 to 3, hours. After the zeolite material has been isolated, for example by filtering off and washing thoroughly, it is advantageously dried, for example at from 100° to 160° C., and calcined at in general from 450° to 600° C. In another preferred embodiment of the acid treatment, the zeolite material is molded with the binder and then treated preferably with from 12 to 20% strength by weight hydrochloric acid at elevated temperatures, advantageously at from 50° to 90° C., preferably from 60° to 80° C., for from 0.5 to 5 hours. The zeolite material is then generally washed thoroughly and advantageously dried, for example at from 100° to 160° C., and calcined at in general from 450° to 600° C. An HF treatment may also be followed by an HCl treatment.

In another procedure, the zeolites can be modified by applying phosphorus compounds, such as trimethyl phosphate, trimethoxyphosphine or primary, secondary or tertiary sodium phosphate. The treatment with primary sodium phosphate has proven particularly advantageous. Here, the zeolites in the form of extrudates, pellets or fluidizable material are impregnated with aqueous $NaH_2PO_4$ solution, dried at 110° C. and calcined at 500° C.

Further catalysts for the preparation of bifunctional building blocks from dialkoxyalkanoates are phosphates, in particular aluminum phosphates, silicon aluminum phosphates, cerium phosphate, zirconium phosphates, boron phosphate, iron phosphate and mixtures thereof.

In particular, substituted and unsubstituted aluminum phosphates and silicon aluminum phosphates synthesized under hydrothermal conditions are used as aluminum phosphate and silicon aluminum phosphate catalysts for the novel process.

The aluminum phosphate catalysts structurally related to the zeolites are synthesized for the novel process, in particular under hydrothermal conditions. In particular they are silicon aluminophosphates (acronym SAPO) or aluminophosphates (acronym $AlPO_4$). These crystalline solids have defined void and pore structures and are structurally related to the zeolites.

The preparation, properties and classification of these solids on the basis of structure and chemical composition are described in detail by R. M. Barrer, Pure and App. Chem., Vol. 58, No. 10, (1986) pages 1317 to 1322, by E. M. Flanigen et al., Pure and Appl. Chem., Vol. 58, No. 10, (1986) pages 1351 to 1358 or by N. B. Milestone et al., Stud. Surf. Sci. Catal. (1988), 36 (Methane Convers.), pages 553 to 562.

About 700 different combinations of the currently known crystal structures and of the many element modifications are now possible. The aluminophosphates are designated by the following acronyms: $AlPO_4$, SAPO, MeAPO, MeAPSO, ElAPO or ElAPSO. A or Al is aluminum, S is silicon, P is phosphorus and 0 is oxygen. Me is a metal, such as Fe, Mg, Mn, Co or Zn, and El is an element, such as Be, Ga, Ge, Ti, As, B or Li. A number added together with a hyphen serves to define the crystal structure of the relevant phase.

The aluminum phosphates prepared under hydrothermal conditions are, for example, AlPO-5, AlPO-9, AlPO-11, AlPO-12, AlPO-14, AlPO-21, AlPO-25, AlPO-31, AlPO-33, AlPO-34, AlPO-37 and AlPO-54. Syntheses of these compounds are described in EP-A-132 708, US-A-4,310,440 and US-A-4,473,663. An overview of this class of compounds is given in Pure and Applied Chemistry 58, 10 (1986), 1351–1358.

For example, $AlPO_4$-5 (APO-5) is synthesized by homogeneously mixing orthophosphoric acid with pseudoboehmite (Catapal ® SB) in water, adding tetrapropylammonium hydroxide to this mixture and then carrying out the reaction in an autoclave at about 150° C. for from 20 to 60 hours under autogenous pressure. The $AlPO_4$ filtered off is dried at from 100° to 160° C. and calcined at from 450° to 550° C.

$AlPO_4$-9 (APO-9) is likewise synthesized from orthophosphoric acid and pseudoboehmite, but in aqueous D.ABCO solution (1,4-diazabicyclo[2.2.2]octane) at about 200° C. under autogenous pressure in the course of from 200 to 400 hours.

$AlPO_4$-21 (APO-21) is synthesized from orthophosphoric acid and pseudoboehmite in aqueous pyrrolidone solution at from 150 to 200° C under autogenous pressure in the course of from 50 to 200 hours.

The syntheses for MeAPOs are described in US-A-4,544,143, EP-A-132 708 and US-A-4,567,029 and those for ElAPO in US-A-4,500,651 and EP-A-158 976.

The silicon-containing aluminophosphates (SAPO, MeAPSO or ElAPSO), such as SAPO-11, SAPO-5, SAPO-20, SAPO-34, SAPO-37, SAPO-41 or SAPO-46, are particularly preferred for the novel process.

Syntheses of the silicon aluminophosphates are described, inter alia, for SAPO in US-A-4,440,871 and EP-A-103 117, for MeAPSO in EP-A-158 348, EP-A-158 975 and EP-A-161 491 and for ElAPSO in EP-A-159 624.

SAPOs are prepared by crystallization from an aqueous mixture at from 100° to 250° C. and under autogenous pressure in the course of from 2 hours to 2 weeks, the reaction mixture comprising a silicon, aluminum and phosphorus component being reacted in aqueous solutions of organic amines.

Examples of suitable silicon aluminophosphates are ZYT-5, ZYT-6, ZYT-7, ZYT-9, ZYT1-11 and ZYT-12 (JP 59/217-619).

For example, SAPO-5 is obtained by mixing $SiO_2$, suspended in aqueous tetrapropylammonium hydroxide solution, with an aqueous suspension of pseudoboehmite and orthophosphoric acid and subsequently carrying out the reaction at from 150° to 200° C. in the course of from 20 to 200 hours under autogenous pressure in a stirred autoclave. Drying of the filtered-off powder is effected at from 110° to 160° C. and calcination at from 450° to 550° C.

Precipitated aluminum phosphates may also be used as phosphate catalysts in the process. For example, an aluminum phosphate of this type is prepared by dissolving 92 g of diammonium hydrogen phosphate in 700 ml of water. 260 g of $Al(NO_3)_3.H_2O$ in 700 ml of water are added dropwise to this solution in the course of 2 hours. The pH is kept at 8 by the simultaneous addition of 25% strength $NH_3$ solution. The precipitate formed is stirred for a further 12 hours and then filtered off under suction and washed thoroughly. It is dried at 60° C. for 16 hours.

Boron phosphates of the novel process can be prepared, for example, by mixing and kneading concentrated boric acid and phosphoric acid and by subsequent drying and calcination in an inert gas, air or steam atmosphere at from 250° to 650° C., preferably from 300° to 500° C.

$CePO_4$ is obtained by precipitation from 52 g of $Ce(NO_3)_3.6H_2O$ and 56 g of $NaH_2PO_4.2H_2O$. After filtration, the material is molded to give extrudates, which are dried at 120° C. and calcined at 450° C. The catalyst contains 47.1% by weight of Ce and 12.7% by weight of P.

Suitable zirconium phosphates are commercial zirconium phosphates, for example CSZ 100, zirconium phosphate silicates and zirconium phosphates which adsorb or which have adsorbed $NH_3$.

These phosphates or phosphates having a zeolite structure can be modified by doping with metals, acid treatment, steaming, etc., as described above for the zeolites.

The catalysts described here can be used alternatively as 2 to 4 mm extrudates or as pellets having a diameter of from 3 to 5 mm or as chips having particle sizes of from 0.1 to 0.5 mm or as a fluidizable catalyst.

In the compounds of the general formulae I, II and III, $R^1$ and $R^2$ independently of one another are each $C_1$-$C_{20}$-alkyl, preferably $C_1$-$C_{12}$-alkyl, such as methyl, ethyl, n-propyl, isopropyl, n-butyl, isobutyl, sec butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl or isododecyl, particularly preferably $C_1$-$C_4$-alkyl, such as methyl, ethyl, n-propyl, isopropyl, n-butyl, isobutyl, sec-butyl or tert-butyl, $C_1$-$C_{20}$-cycloalkyl, preferably $C_3$-$C_8$-cycloalkyl, such as cyclopropyl, cyclobutyl, cyclopentyl, cyclohexyl, cycloheptyl or cyclooctyl, particularly preferably cyclopentyl, cyclohexyl or cyclooctyl, $C_4$-$C_{20}$-alkylcycloalkyl, preferably $C_6$-$C_{20}$-alkylcycloalkyl, such as 2-methylcyclopentyl, 3-methylcyclohexyl or 4-methylcyclohexyl, $C_4$-$C_{20}$-cycloalkylalkyl, preferably $C_6$-$C_{20}$-cycloalkylalkyl, such as cyclopentylmethyl, cyclohexylmethyl or cyclohexylethyl, aryl, such as phenyl, 1-naphthyl, 2-naphthyl, 1-anthryl, 2-anthryl or 9-anthryl, preferably phenyl, 1-naphthyl or 2-naphthyl, particularly preferably phenyl, $C_7$-$C_{20}$-alkylaryl, preferably $C_7$-$C_{12}$-alkylphenyl, such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl or 4-n-propylphenyl, $C_7$–$C_{20}$-aralkyl, preferably $C_7$–$C_{12}$-phenylalkyl, such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl or 4-phenylbutyl, particularly preferably benzyl, 1-phenethyl or 2-phenethyl, or a heterocyclic radical, such as an aromatic or a nonaromatic heterocyclic structure having from one to three hetero atoms, such as nitrogen, oxygen and/or sulfur, preferably nitrogen and oxygen, and n is an integer of from 3 to 7, such as 3, 4, 5, 6 or 7, preferably 4 or 5.

Examples of preferred ketones II are: acetophenone, benzophenone, phenylacetone, methyl isopropyl ketone, 2-butanone, 2-pentanone, 3-pentanone, hexanone, cyclohexanone and cyclopentanone.

Examples of preferred cyclic amines III are: pyrrolidine, morpholine and piperidine.

The preparation of such starting materials of the formulae II and III is sufficiently well known from standard works (Beilstein, Gmelin).

The amines I are, as a rule, useful building blocks in organic synthesis. Such compounds are of particular interest as intermediates for drugs and active ingredients in herbicides, fungicides and insecticides and as catalysts for organic synthesis or in polymerizations.

The Examples which follow illustrate the invention.

Gas-phase reaction

The reactions in the gas phase are carried out under isothermal conditions in a tubular reactor (coil, 0.6 cm internal diameter, 90 cm length) over a fixed-bed catalyst. The amount of catalyst was varied from 1 to 20 g, corresponding to a space velocity WHSV of from 0.1 to 10 $h^{-1}$. The reaction products are isolated by conventional methods and characterized by GC/MS. The quantitative determination of the reaction products and of the starting materials was carried out by gas chromatography or by weighing the fractions obtained by distillation or extraction.

The catalysts used for the novel process are:

Catalyst A

The borosilicate zeolite of the pentasil type is prepared in a hydrothermal synthesis from. 640 g of finely divided $SiO_2$, 122g of $H_3BO_3$, 8,000 g of an aqueous 1,6-hexanediamine solution (weight ratio of the mixture 50 : 50 ) at 170° C. under autogenous pressure in a stirred autoclave. The crystalline reaction product is filtered off, washed thoroughly and then dried at 100° C. for 24 hours and calcined at 500° C. for 24 hours.

This borosilicate zeolite is composed of 94.2% by weight of $SiO_2$ and 2.3% by weight of $B_2O_3$.

This material is molded with boehmite as a binder (weight ratio 60 : 40) to give 2 mm extrudates, which are dried at 110° C. for 166 hours and calcined at 500° C. for 24 hours.

Catalyst A is obtained by subjecting these extrudates to ion exchange with ammoniacal palladium nitrate solution and then carrying out drying at 110° C. for 16 hours and calcination at 500° C. for 5 hours. The Pd content is 3.3% by weight.

Catalyst B

The borosilicate zeolite of the pentasil type molded with boehmite (cf. catalyst A) is impregnated with an aqueous $AgNO_3$ solution. Thereafter, drying is carried out at 130° C. for 2 hours and calcination at 540° C. for 2 hours.

Catalyst C

The borosilicate zeolite of the pentasil type molded with boehmite (cf. catalyst A) is treated with a 20% strength aqueous $NH_4Cl$ solution at 80° C. for 2 hours. It is then washed Cl-free. Treatment is then carried out with an ammoniacal Pd nitrate solution at 50° C. for 16 hours in a circulation apparatus. After drying at 110° C. for 2 hours and calcination at 500° C. for 5 hours, the Pd content is 0.34% by weight.

Catalyst D

Borosilicate zeolite powder is prepared as described for catalyst A and subjected to ion exchange at 50° C. for 4 hours with an ammoniacal Pd nitrate solution and an $NaNO_3$ solution. Thereafter, drying is carried out at 110° C. for 2 hours and calcination at 500° C. for 5 hours. The Pd content of the zeolite after ion exchange is 0.45% by weight and the Na content is 0.12% by weight. This powder is molded with molding assistants at a molding pressure of 110 bar to give 2.5 mm extrudates. The extrudates are dried at 100° C. for 2 hours and calcined at 500° C. for 16 hours.

Catalyst E

The borosilicate zeolite of the pentasil type molded with boehmite (cf. catalyst A) is impregnated with an ammoniacal Pt chloride solution. Thereafter, drying is carried out at 130° C. for 2 hours and calcination at 540° C. for 2 hours. The Pd content is then 2.49% by weight.

Catalyst F

Borosilicate zeolite powder is prepared as described for catalyst A and subjected to ion exchange at 50° C. for 4 hours with an ammoniacal Pt chloride solution. The product is filtered off and washed thoroughly with $H_2O$ and then dried at 110° C. for 2 hours and calcined at 500° C. for 5 hours. The Pt content is then 2.11% by weight.

Catalyst G

An aluminosilicate zeolite of the pentasil type is prepared under hydrothermal conditions, at autogenous pressure and 150° C., from 65 g of finely divided $SiO_2$, and 20.3 g of $Al_2(SO_4)_3.18H_2O$ in 1 kg of an aqueous 1,6-hexanediamine solution (weight ratio of the mixture 50 : 50 ) in a stirred autoclave. The crystalline reaction product is filtered off, washed thoroughly and dried at 110° C. for 24 hours and calcined at 500° C. for 24 hours. This aluminosilicate zeolite contains 91.6% by weight of $SiO_2$ and 4.6% by weight of $Al_2O_3$. The catalyst is molded with a molding assistant to give 2 mm extrudates, which are dried at 110° C. for 16 hours and calcined at 500° C. for 24 hours.

These extrudates are impregnated with an aqueous solution of Cu nitrate, Ni nitrate and Pd chloride. After drying at 130° C. for 2 hours and calcination at 540° C. for 2 hours, the Cu content is 2.6% by weight, the Ni content is 0.57% by weight, the Pd content is 0.05% by weight and the Cl content is 0.06% by weight.

Catalyst H

Commercial Na Y zeolite is molded with boehmite in a weight ratio of 60 : 40 at a molding pressure of 100 bar to give 2 mm extrudates, which are dried at 110° C. for 2 hours and calcined at 500° C. for 16 hours. These extrudates are subjected to ion exchange with an ammoniacal Pd nitrate solution at 50° C. After drying at 110° C. for 2 hours and calcination at 500° C. for 5 hours, the Pd content is 2.33% by weight and the Na content is 3.6% by weight.

Catalyst I

Na Y zeolite extrudates are subjected to ion exchange with a 20% NH Cl solution at 80° C. for 2 hours, as described for catalyst H. This exchange is repeated 3 times. After drying at 110° C. for 2 hours and calcination at 500° C. for 5 hours, the Na content is 0.2% by weight. Ion exchange is now effected with an aqueous Co nitrate solution at 80° C. for 2 hours. Thorough washing with $H_2O$ is followed by drying at 130° C. for 2 hours and calcination at 540° C. for 2 hours.

Catalyst J

The HY-zeolite prepared as catalyst J by ion exchange (but without molding with boehmite) is treated with an aqueous Cu nitrate solution and molded with a molding assistant to give 2 mm extrudates, which are dried at 130° C. for 2 hours and calcined at 540° C. for 2 hours. The Cu content is 5% by weight.

Catalyst K 13X molecular sieve available commercially from Union Carbide and having an $SiO_2$ content of 46.5% by weight, an $Al_2O_3$ content of 27.9% by weight and an Na content of 11.3% by weight is subjected to ion exchange in a column with 20% strength aqueous Cu nitrate solution at 80° C. for 2 hours. Thereafter, it is washed $NO_3$-free, dried at 110° C. for 2 hours and calcined at 500° C. for 5 hours. The Cu content is 13.9% by weight and the Na content 1.3% by weight.

Catalyst L

Beta-zeolite available commercially from PQ Corporation and having an $SiO_2$ content of 87.0% by weight and an $Al_2O_3$ content of 4.9% by weight is subjected to ion exchange with an ammoniacal Pd nitrate solution at 50° C. for 4 hours. The product is filtered off and then dried at 110° C. for 2 hours and calcined at 500° C. for 5 hours. The Pd content is 2.73% by weight. This powder is molded with molding assistants to give 2 mm extrudates, dried at 110° C. and calcined at 500° C. for 16 hours.

Catalyst M $AlPO_4$-5 (APO-5) is synthesized by dissolving or suspending 200 g of 98% strength phosphoric acid and 136 g of boehmite in 335 g of water, adding 678 g of a 30% strength aqueous tetrapropylammonium hydroxide solution and reacting this mixture at 150° C. under autogenous pressure for 43 hours in a stirred autoclave. The crystalline material is filtered off and then dried at 120° C. and calcined at 500° C. for 16 hours. The $AlPO_4$-5 synthesized in this manner contains 45.5% by weight of $Al_2O_3$ and 46.5% by weight of $P_2O_5$. This material is treated with an aqueous Rh nitrate solution and molded with molding assistants to give 2 mm extrudates, which are dried at 120° C. and calcined at 500° C. for 16 hours. The Rh content is 2% by weight.

Catalyst N

Silicon aluminophosphate-5 (SAPO-5) is prepared from a mixture of 200 g of 98% strength phosphoric acid, 136 g of boehmite, 60 g of 30% strength silica sol, 287 g of tripropylamine and 587 g of $H_2O$. This mixture is reacted at 150° C. under autogenous pressure for 168 hours. The crystalline product is filtered off and then dried at 120° C. and calcined at 500° C. SAPO-5 contains 49.8% by weight of $P_2O_5$, 33.0% by weight of $Al_2O_3$ and 6.2% by weight of $SiO_2$. SAPO-5 is molded with finely divided silica gel in a weight ratio of 80 : 20 to give 2 mm extrudates, which are dried at 110° C. and calcined at 500° C. for 16 hours. These extrudates are subjected to ion exchange with ammoniacal Pd nitrate solution at 50° C. After drying at 110° C. for 2 hours and calcination at 500° C. for 16 hours, the Pd content is 0.5% by weight.

Catalyst O

An SAPO-11 is synthesized by homogeneously mixing 200 g of orthophosphoric acid (98% by weight) with 417 g of aluminum triisopropylate and 60 g of silica sol (30% by weight of $SiO_2$) in 927 g of water and adding 91.5 g of di-n-propylamine to this mixture. The reaction is then carried out at 200° C. under autogenous pressure for 96 hours in a stirred autoclave. The silicon aluminophosphate is filtered off, washed, dried at 110° C. and calcined at 500° C. The SAPO-11 is composed of 40.4% by weight of $Al_2O_3$, 49.5% by weight of $P_2O_5$ and 1.87% by weight of $SiO_2$. This material is molded with a molding assistant to give 2 mm extrudates which are dried at 110° C. for 16 hours and calcined at 500° C. for 16 hours. These extrudates are subjected to ion exchange with an ammoniacal Pd nitrate solution at 50° C. After drying at 110° C. for 2 hours and calcination at 500° C. for 16 hours, the Pd content is 0.5% by weight.

Catalyst P

SAPO-34 commercially available from Union Carbide Corporation is molded with pyrogenic silica gel in a weight ratio of 80 : 20 to give 2 mm extrudates, which are dried at 110° C. and calcined at 500° C. for 16 hours. These extrudates are subjected to ion exchange with an ammoniacal Pd nitrate solution at 50° C. After filtration, drying is carried out at 110° C. for 2 hours and calcination at 500° C. for 16 hours. The Pd content is 0.5% by weight.

The experimental results obtained with these catalysts are listed in the Tables below.

Reaction A: Benzophenone + pyrrolidine →
Reaction B: Methyl isopropyl ketone + morpholine →

Reaction C: Methyl isopropyl ketone + piperidine →
Reaction D: Methyl isopropyl ketone + pyrrolidine →

Reaction E: 2-Pentanone + morpholine →
Reaction F: 2-Pentanone + piperidine →
Reaction G: 2-Pentanone + pyrrolidine →
Reaction H: 2-Pentanone + 2,6-dimethylpiperidine →
Reaction I: 2-Pentanone + 4-methylpiperidine →

TABLE 1

Catalyst screening for reactions A–G

| Example | Catalyst | Reaction | Temp. °C. | WHSV $h^{-1}$ | $H_2$ ml/min | Conversion % based on ketone | Selectivity % based on product |
|---|---|---|---|---|---|---|---|
| 1 | A | A | 170 | 1 | 64 | 49.5 | 62.7 |
| 2 | A | B | 180 | 1.4 | 64 | 40.8 | 79.7 |
| 3 | A | C | 150 | 0.7 | 32 | 14.2 | 71.1 |
| 4 | A | C | 180 | 0.7 | 32 | 50.1 | 78.3 |
| 5 | A | C | 180 | 1.4 | 64 | 46.1 | 74.1 |
| 6 | A | C | 200 | 2.3 | 128 | 30.4 | 60.1 |
| 7 | A | E | 160 | 1.5 | 64 | 36.7 | 86.0 |
| 8 | A | E | 170 | 1.4 | 64 | 85.8 | 97.0 |
| 9 | A | E | 180 | 1.5 | 64 | 83.5 | 97.2 |
| 10 | A | E | 190 | 1.5 | 64 | 75.1 | 93.6 |
| 11 | B | E | 170 | 1.4 | 64 | 18.4 | 69.2 |
| 12 | B | E | 200 | 1.4 | 64 | 14.4 | 63.6 |
| 13 | C | E | 170 | 1.5 | 64 | 73.2 | 98.2 |
| 14 | D | B | 170 | 1.2 | 64 | 10.4 | 71.0 |
| 15 | D | C | 170 | 1.3 | 64 | 14.3 | 79.2 |
| 16 | D | E | 170 | 1.6 | 64 | 45.2 | 93.6 |
| 17 | D | F | 170 | 1.3 | 64 | 66.7 | 96.8 |
| 18 | E | E | 170 | 1.5 | 64 | 70.0 | 99.0 |
| 19 | F | E | 170 | 1.0 | 64 | 55.8 | 98.3 |
| 20 | G | E | 170 | 1.7 | 64 | 17.0 | 89.2 |
| 21 | H | E | 170 | 0.8 | 32 | 62.7 | 94.8 |
| 22 | H | E | 170 | 1.4 | 64 | 75.7 | 96.2 |
| 23 | H | B | 180 | 1.4 | 64 | 33.0 | 90.2 |
| 24 | J | E | 170 | 1.5 | 64 | 6.5 | 37.5 |
| 25 | I | E | 170 | 1.5 | 64 | 15.3 | 82.8 |
| 26 | J | E | 170 | 1.5 | 64 | 23.0 | 94.7 |
| 27 | K | E | 220 | 1.4 | 64 | 13.6 | 87.6 |
| 28 | K | H | 170 | 1.2 | 64 | 7.4 | 41.3 |
| 29 | L | I | 170 | 1.4 | 64 | 71.3 | 98.4 |
| 30 | L | A | 170 | 0.9 | 64 | 44.9 | 58.8 |
| 31 | L | B | 170 | 1.5 | 64 | 33.5 | 95.7 |
| 32 | L | C | 170 | 1.4 | 64 | 55.0 | 93.8 |
| 33 | L | D | 170 | 1.5 | 64 | 41.1 | 95.4 |
| 34 | M | E | 170 | 1.3 | 64 | 46.0 | 97.6 |
| 35 | N | E | 170 | 1.4 | 64 | 42.5 | 97.7 |
| 36 | O | E | 170 | 1.4 | 64 | 63.6 | 98.8 |
| 37 | P | E | 170 | 1.5 | 64 | 50.4 | 97.4 |

TABLE 2

Catalyst L, reaction F, 170° C., WHSV = 1.4 $h^{-1}$, 64 ml/min $H_2$
EXAMPLE 38

| Time [h] | Conversion Educt 1 | Selectivities Product |
|---|---|---|
| 1.25 | 88.42 | 97.88 |
| 2.25 | 89.77 | 99.63 |
| 4.25 | 89.01 | 99.50 |
| 8.25 | 86.18 | 98.80 |
| 12.25 | 85.31 | 98.22 |
| 16.25 | 84.35 | 98.73 |
| 20.25 | 83.85 | 98.57 |
| 24.25 | 83.53 | 99.00 |
| 28.25 | 82.07 | 98.70 |
| 32.25 | 81.88 | 98.11 |
| 36.25 | 81.46 | 98.09 |
| 40.25 | 81.72 | 97.95 |
| 44.25 | 81.58 | 98.24 |
| 48.25 | 81.29 | 97.94 |
| 52.25 | 80.12 | 98.03 |
| 56.25 | 79.98 | 98.18 |
| 60.25 | 79.83 | 98.02 |
| 48.25 | 81.29 | 98.08 |
| 60.50 | — | — |
|  | 83.43 | 98.43 |

TABLE 3

Catalyst L, reaction G, 170° C., WHSV = 1.2 $h^{-1}$, 64 ml/min $H_2$
EXAMPLE 39

| Time [h] | Conversion Educt 1 | Selectivities Product |
|---|---|---|
| 0.25 |  |  |
| 1.25 | 79.51 | 91.27 |
| 2.25 | 86.76 | 96.92 |
| 4.25 | 88.58 | 96.78 |
| 8.25 | 89.81 | 96.95 |
| 12.25 | 90.43 | 97.48 |
| 16.25 | 90.66 | 97.01 |
| 20.25 | 90.54 | 97.36 |
| 24.25 | 90.38 | 97.58 |
| 28.25 | 89.18 | 96.32 |
| 32.25 | 88.68 | 96.03 |
| 36.25 | 88.67 | 95.91 |
| 40.25 | 88.77 | 95.91 |
| 44.25 | 88.63 | 95.64 |
| 48.25 | 88.51 | 95.51 |
| 52.25 | 86.96 | 96.03 |
| 56.25 | 86.70 | 96.80 |
| 60.25 | 86.68 | 96.54 |
| 48.25 | 88.38 | 95.49 |
| 60.25 | — | — |
|  | 88.73 | 96.49 |

TABLE 4

Catalyst L, reaction G, 170° C., WHSV = 1.4 $h^{-1}$, 64 ml/min $H_2$
EXAMPLE 40

| Time [h] | Conversion Educt 1 | Selectivities Product |
|---|---|---|
| 0.25 |  |  |
| 1.25 | 90.39 | 98.87 |
| 2.25 | 92.30 | 97.00 |
| 4.25 | 88.75 | 99.30 |
| 8.25 | 87.64 | 97.63 |
| 12.25 | 86.81 | 99.52 |
| 16.25 | 84.92 | 99.25 |
| 20.25 | 85.79 | 99.75 |
| 24.25 | 85.38 | 100.00 |
| 28.25 | 84.80 | 98.52 |
| 32.25 | 84.68 | 98.51 |
| 36.25 | 67.90 | 81.82 |
| 40.25 | 84.42 | 98.50 |
| 44.25 | 84.18 | 97.99 |
| 48.25 | 83.76 | 98.49 |
| 52.25 | 83.72 | 98.60 |
| 56.25 | 83.76 | 98.47 |
| 60.25 | 83.40 | 98.33 |
| 48.25 | 83.65 | 98.49 |
| 60.25 | — | — |
|  | 85.49 | 98.62 |

We claim:

1. A process for the preparation of an amine of the formula

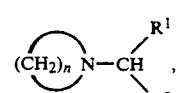

I wherein:
n is an integer of from 3 to 7 and the alkylene chain —$(CH_2)_n$— is optionally substituted once or twice by methyl, or when n is 4, said alkylene chain is optionally interrupted by an oxygen atom to form a morpholine ring, and $R^1$ and $R^2$ are each $C_1$–$C_{20}$-alkyl, $C_3$–$C_{20}$-cycloalkyl, $C_4$–$C_{20}$-alkylcycloalkyl, $C_4$–$C_{20}$-cycloalkylalkyl, aryl, $C_7$–$C_{20}$-alkylaryl, $C_7$–$C_{20}$-aralkyl or a heterocyclic radical which has an aromatic or nonaromatic heterocyclic structure with one to three nitrogen, oxygen or sulfur atoms, which process comprises:
reacting a ketone of the formula

(II)

with a cyclic amine of the formula

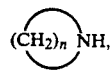
III wherein n and the alkylene chain —$(CH_2)_n$— have the above meanings, in the presence of a zeolite of $SiO_2$ having a zeolite structure or a phosphate or a phosphate having a zeolite structure as a catalyst, at a temperature of from 50° to 500° C. and under a pressure of from 0.01 to 50 bar.

2. A process as claimed in claim 1, wherein the catalyst used is a zeolite of the pentasil, faujasite, mordenite or beta type.

3. A process as claimed in claim 1, wherein the catalyst used is an aluminosilicate, gallosilicate, borosilicate or ferrosilicate zeolite.

4. A process as claimed in claim 1, wherein the catalyst used is a zeolite doped with noble metals, alkali metals, transition metals or rare earth metals.

5. A process as claimed in claim 4, wherein the metals used for doping are Pd, Pt, Rh, Re, Ru, Co, CU, Cr, Fe, Ag and Zn.

6. A process as claimed in claim 1, wherein the catalyst used is a phosphate of the element B, Al, Zr, Fe or Sr or of a mixture thereof.

7. A process as claimed in claim 1, wherein the catalyst used is a hydrothermally prepared phosphate which has a zeolite structure.

8. A process as claimed in claim 7, wherein the catalyst used is a hydrothermally prepared aluminum phosphate or silicon aluminophosphate having a zeolite structure, which may additionally contain the elements lithium, beryllium, boron, magnesium, gallium, germanium, arsenic, titanium, manganese, iron, cobalt or zinc.

9. A process as claimed in claim 7, wherein the hydrothermally prepared phosphate is selected from the group consisting of $AlPO_4$, SAPO, ElAPO, ElAPSO, MeAPO or MeAPSO.

10. A process as claimed in claim 1, wherein the reaction is carried out in the gas phase.

11. A process as claimed in claim 1, wherein n in the formulas I and III is an integer of from 4 to 5.

12. A process as claimed in claim 11, wherein $R^1$ and $R^2$ independently of one another are each $C_1$–$C_{12}$-alkyl, $C_3$–$C_8$-cycloalkyl, $C_6$–$C_{20}$-alkylcycloalkyl, $C_6$–$C_{20}$ cycloalkylalkyl, phenyl, $C_7$–$C_{12}$-alkylphenyl, $C_7$–$C_{12}$-phenylalkyl, 1-naphthyl, 2-naphthyl, 1-anthryl, 2-anthryl, 9-anthryl, or a heterocyclic radical which has an aromatic or nonaromatic heterocyclic structure with one to three nitrogen or oxygen atoms.

13. A process as claimed in claim 1, wherein the cyclic amine III is selected from the group consisting of pyrollidone, morpholine, piperidine, 2,5-dimehtylpiperidine and 4-methylpiperidine.

* * * * *